United States Patent
Iselborn et al.

(10) Patent No.: US 11,384,037 B2
(45) Date of Patent: Jul. 12, 2022

(54) METHOD FOR REMOVING DIENES FROM A MATERIAL STREAM CONTAINING C3 TO C5 HYDROCARBONS BY SELECTIVE HYDROGENATION

(71) Applicant: BASF SE, Ludwigshafen am Rhein (DE)

(72) Inventors: Stefan Iselborn, Ludwigshafen am Rhein (DE); Andreas Joerg Ufer, Ludwigshafen am Rhein (DE); Joachim Koetter, Markkleeberg (DE)

(73) Assignee: BASF SE, Ludwigshafen am Rhein (DE)

( * ) Notice: Subject to any disclaimer, the term of this patent is extended or adjusted under 35 U.S.C. 154(b) by 6 days.

(21) Appl. No.: 16/759,095

(22) PCT Filed: Oct. 25, 2018

(86) PCT No.: PCT/EP2018/079250
§ 371 (c)(1),
(2) Date: Apr. 24, 2020

(87) PCT Pub. No.: WO2019/081628
PCT Pub. Date: May 2, 2019

(65) Prior Publication Data
US 2021/0179518 A1    Jun. 17, 2021

(30) Foreign Application Priority Data
Oct. 25, 2017  (EP) ..................................... 17198380

(51) Int. Cl.
*C07C 7/163*  (2006.01)

(52) U.S. Cl.
CPC .......... *C07C 7/163* (2013.01); *C07C 2523/50* (2013.01)

(58) Field of Classification Search
CPC . C07C 7/163; C07C 2523/44; C07C 2523/50; C07C 2523/52; C07C 11/08
See application file for complete search history.

(56) References Cited

U.S. PATENT DOCUMENTS

| | | |
|---|---|---|
| 2,882,243 A | 4/1959 | Milton |
| 2,934,574 A | 4/1960 | Viland |
| 3,481,999 A | 12/1969 | Reich |
| 3,992,471 A | 11/1976 | Priegnitz |
| 4,190,520 A * | 2/1980 | Gewartowski ........ C07C 5/2702 208/100 |
| 4,260,840 A * | 4/1981 | Puls ........................ C07C 7/163 585/259 |
| 4,567,309 A | 1/1986 | Kulprathipanja |
| 6,118,034 A | 9/2000 | Kons et al. |
| 6,169,218 B1 | 1/2001 | Hearn et al. |
| 7,923,588 B2 | 4/2011 | Stephan et al. |
| 8,067,334 B2 | 11/2011 | Hill et al. |
| 2009/0030250 A1* | 1/2009 | Hill ......................... C07C 7/163 585/273 |
| 2010/0228063 A1* | 9/2010 | Almering ................ C07C 7/163 585/264 |
| 2011/0071328 A1 | 3/2011 | Riley et al. |

FOREIGN PATENT DOCUMENTS

| | | |
|---|---|---|
| DE | 0111197 | 6/1900 |
| DE | 111197 A1 | 2/1975 |
| DE | 3301164 A1 | 7/1984 |
| RU | 2145952 C1 | 2/2000 |
| RU | 2180678 C2 | 3/2002 |
| RU | 2442766 C1 | 2/2012 |
| WO | WO-2006040159 A1 | 4/2006 |
| WO | WO-2006040160 A1 | 4/2006 |
| WO | WO-2006124167 A2 | 11/2006 |
| WO | WO-2014209736 A1 | 12/2014 |
| WO | WO-2015170282 A1 | 11/2015 |

OTHER PUBLICATIONS

International Search Report for PCT/EP2018/079250 dated Dec. 20, 2018.
Written Opinion of the International Searching Authority for PCT/EP2018/079250 dated Dec. 20, 2018.

* cited by examiner

*Primary Examiner* — Youngsul Jeong
*Assistant Examiner* — Jason Y Chong
(74) *Attorney, Agent, or Firm* — Faegre Drinker Biddle & Reath LLP

(57) ABSTRACT

The invention relates to a process for removing dienes from a material stream comprising $C_3$ to $C_5$ hydrocarbons by selective hydrogenation at a specified reaction pressure and a specified reaction temperature in the presence of a hydrogenation catalyst, wherein the reaction pressure and the reaction temperature at the reactor inlet are regulated such that the reaction pressure at the reactor inlet does not deviate by more than 0.01 bar from the specified reaction pressure and the reaction temperature at the reactor inlet does not deviate by more than 0.1° C. from the specified reaction temperature and the proportion of hydrogen supplied to the selective hydrogenation is in the range from 2 to 20 moles per mole of diene present in the material stream comprising $C_3$ to $C_5$ hydrocarbons.

13 Claims, No Drawings

METHOD FOR REMOVING DIENES FROM A MATERIAL STREAM CONTAINING C3 TO C5 HYDROCARBONS BY SELECTIVE HYDROGENATION

CROSS-REFERENCE TO RELATED APPLICATIONS

This application is a national stage application (under 35 U.S.C. § 371) of PCT/EP2018/079250, filed Oct. 25, 2018, which claims benefit of European Application No. 17198380.2, filed Oct. 25, 2017, both of which are incorporated herein by reference in their entirety.

DESCRIPTION

The basis of the invention is a process for removing dienes from a material stream comprising $C_3$ to $C_5$ hydrocarbons by selective hydrogenation.

Selective hydrogenation converts the dienes into alkenes having one double bond or into the corresponding alkanes, thereby removing them from the material stream.

Alkenes having one double bond are used, for example, as monomers or co-monomers in polymer production. But-1-ene is a typical compound for such a use.

Material streams that comprise the desired compounds generally also comprise secondary components formed, for example, as unwanted by-products during production. Some of the byproducts can be separated from the crude product by conventional purification processes, for example distillative methods of separation. However, this is not always possible in a straightforward manner, particularly in the case of secondary components with boiling points close to that of the desired product. In particular, residual amounts of butadiene are generally still present during the production and purification of but-1-ene. However, this has the disadvantage that when but-1-ene is used as a monomer in polymer production, even these small amounts of butadiene can cause problems, since the butadiene affects polymer cross-linking.

Because of the similar boiling point, the butadiene is usually removed by selective hydrogenation. This is able to further reduce the proportion of butadiene in the product stream. However, a drawback of selective hydrogenation is that, in addition to the but-1-ene formed by the hydrogenation, but-2-ene and other unwanted by-products can also form. The formation of these byproducts in turn has the disadvantage that the desired concentration of but-1-ene in the product stream may not necessarily be attained.

A process for removing butadiene by selective hydrogenation from material streams comprising but-1-ene and butadiene is described, for example, in U.S. Pat. No. 4,260,840, WO-A 2015/170282, WO-A 2006/124167, U.S. Pat. No. 3,481,999 or DE-A 33 01 164.

To reduce losses of the desired target product, but-1-ene, DE-A 33 01 164 and WO-A 2006/124167 disclose that the reaction should be carried out in the presence of small amounts of carbon monoxide. Losses of the desired target product can arise, for example, from the reaction of the hydrogen added for the selective hydrogenation not only with the butadiene but with the but-1-ene too. The result of this, possibly on account of the selective hydrogenation and the by-products formed thereby, is that the target specification for the content of the target product in the material stream is no longer achieved. Particularly when there is a low diene content in a material stream that comprises the target product in high purity, the proportion of by-products formed by selective hydrogenation is generally so high that the concentration of the target product after the selective hydrogenation no longer meets the required specifications.

In addition to the removal of dienes by selective hydrogenation, the removal of dienes from a material stream by adsorption processes is also known. This is done using, for example, molecular sieves or zeolites that preferentially adsorb the substances to be removed. Such adsorption processes are disclosed for example in U.S. Pat. Nos. 4,567,309, 2,882,243, 3,992,471, and DD-A 111 197.

However, these processes too all have the disadvantage of not permitting the removal of very small amounts of dienes from the material stream.

It was therefore an object of the present invention to provide a process with which dienes can be removed from a material stream comprising $C_3$ to $C_5$ hydrocarbons and with which the concentration of products of value is kept within a predefined specification.

This object is achieved by a process for removing dienes from a material stream comprising $C_3$ to $C_5$ hydrocarbons by selective hydrogenation at a specified reaction pressure and a specified reaction temperature in the presence of a hydrogenation catalyst, wherein the reaction pressure and the reaction temperature at the reactor inlet are regulated such that the reaction pressure at the reactor inlet does not deviate by more than 0.01 bar from the specified reaction pressure and the reaction temperature at the reactor inlet does not deviate by more than 0.1° C. from the specified reaction temperature and the proportion of hydrogen supplied to the selective hydrogenation is in the range from 2 to 20 moles per mole of diene present in the material stream comprising $C_3$ to $C_5$ hydrocarbons.

When carrying out the selective hydrogenation such that the reaction pressure at the reactor inlet does not deviate by more than 0.01 bar from the specified reaction pressure and the reaction temperature at the reactor inlet does not deviate by more than 0.1° C. from the specified reaction temperature, it was surprisingly found that unwanted side reactions, and thus the formation of by-products that can result in a desired specification for product purity not being met, can be prevented or reduced. The process according to the invention thus makes it possible to carry out the selective hydrogenation in a way that avoids or at least significantly reduces overhydrogenation, that is to say hydrogenation or isomerization of the desired target product through which the content of the target product in the material stream decreases, potentially resulting in failure to reach the target product concentration needed for the required specification.

Regulation of the reaction temperature and reaction pressure is achieved, for example, by a process for removing dienes from a material stream comprising $C_3$ to $C_5$ hydrocarbons by selective hydrogenation that comprises the following steps:

(a) vaporizing part of a material stream comprising liquid $C_3$ to $C_5$ hydrocarbons, mixing a gaseous material stream comprising $C_3$ to $C_5$ hydrocarbons and a liquid one, or condensing part of a material stream comprising gaseous $C_3$ to $C_5$ hydrocarbons, with the result that 2 to 50 mol %, preferably 3 to 30 mol %, and in particular 5 to 25 mol %, of the material stream comprising $C_3$ to $C_5$ hydrocarbons is present in the gas phase after vaporization, (b) supplying the partially vaporized material stream comprising $C_3$ to $C_5$ hydrocarbons to a reaction step comprising a hydrogenation catalyst and adding hydrogen in a proportion of 2 to 20 moles per mole of diene present in the material stream comprising $C_3$ to $C_5$ hydrocarbons, wherein the hydrogen may be added together with the partially vaporized material stream comprising $C_3$ to $C_5$ hydrocarbons or via a separate addition point, (c) separating the gas phase and liquid phase and withdrawing the liquid phase as a product stream.

By vaporizing part of the material stream comprising $C_3$ to $C_5$ hydrocarbons or alternatively by splitting the material stream comprising $C_3$ to $C_5$ hydrocarbons into two material streams, vaporizing one of the two material streams, and then mixing the two material streams, by mixing a gaseous material stream comprising $C_3$ to $C_5$ hydrocarbons and a liquid one, or by condensing part of the material stream comprising $C_3$ to $C_5$ hydrocarbons such that a material stream is generated in which 2 to 50 mol %, preferably 3 to 30 mol %, and in particular 5 to 25 mol %, is present in the gas phase, it is possible to keep within very narrow process conditions, i.e. a reaction pressure at the reactor inlet that does not deviate by more than 0.01 bar from a specified reaction pressure and a reaction temperature at the reactor inlet that does not deviate by more than 0.1° C. from a specified reaction temperature, that allow selective hydrogenation to be carried out without overhydrogenation occurring. This makes it possible to meet the desired specification for the concentration of products of value.

Unlike with direct control of the temperature or pressure, it is possible, by vaporizing part of the material stream comprising $C_3$ to $C_5$ hydrocarbons that is used, mixing a gaseous material stream comprising $C_3$ to $C_5$ hydrocarbons and a liquid one, or condensing part of the material stream comprising $C_3$ to $C_5$ hydrocarbons, for the reaction conditions to be kept within the required window with far easier control. For example, small changes in the size of the vaporized substream do not immediately lead to changes in pressure and temperature in the reactor. Unlike the windows for temperature and pressure within which the desired product specification is achieved, the window for partial vaporization is broader, which provides the necessary time for parameters to be corrected and does not lead to the desired product specification no longer being achieved during such parameter correction.

When part of the material stream comprising $C_3$ to $C_5$ hydrocarbons is vaporized, the gaseous proportion of the material stream comprising $C_3$ to $C_5$ hydrocarbons that is used may be adjusted either by regulating the supplied heat flow or else by splitting the material stream comprising $C_3$ to $C_5$ hydrocarbons, vaporizing a part thereof, and then mixing the two substreams.

A further option for adjusting the gaseous proportion of the material stream comprising $C_3$ to $C_5$ hydrocarbons in step (a), with the result that 2 to 50 mol %, preferably 3 to 30 mol %, and in particular 5 to 25 mol %, of the material stream comprising $C_3$ to $C_5$ hydrocarbons is present in the gas phase, is to add an inert gas. Adding the inert gas lowers the partial pressure of the individual components in the material stream comprising $C_3$ to $C_5$ hydrocarbons, thereby providing a means of adjusting the vaporization temperature and the vaporized part of the material stream comprising $C_3$ to $C_5$ hydrocarbons.

The inert gas may be added before, during or after vaporizing part of a liquid material stream comprising $C_3$ to $C_5$ hydrocarbons, mixing a gaseous material stream comprising $C_3$ to $C_5$ hydrocarbons and a liquid one, or condensing part of a gaseous material stream comprising $C_3$ to $C_5$ hydrocarbons in step (a). When a gaseous material stream comprising $C_3$ to $C_5$ hydrocarbons and a liquid one are mixed, it is possible to add the inert gas to the liquid material stream only, to the gaseous material stream only, or else to both material streams comprising $C_3$ to $C_5$ hydrocarbons.

When adding the inert gas during vaporization, mixing or condensing, it is possible for this to be added, for example via a separate infeed, to the apparatus in which vaporization, mixing or condensing is carried out.

Examples of suitable inert gases that can be added during vaporization are selected from the group consisting of nitrogen, methane, carbon dioxide, noble gases, and mixtures thereof. Particular preference as inert gases is given to methane and nitrogen.

The proportion of inert gas to be added is regulated such that the amount of inert gas is increased if the proportion of the gaseous material stream comprising $C_3$ to $C_5$ hydrocarbons is too low and decreased if the proportion of the gaseous material stream comprising $C_3$ to $C_5$ hydrocarbons is too high.

It is particularly preferable when the material stream comprising $C_3$ to $C_5$ hydrocarbons that is used is liquid and the gaseous proportion is achieved by vaporizing part of the material stream comprising $C_3$ to $C_5$ hydrocarbons.

The proportion of the gas phase of the material stream comprising $C_3$ to $C_5$ hydrocarbons is determined, for example, at the outlet from the evaporator. It is possible to use for this purpose any suitable sensor with which the amount in the gas phase can be determined. This can be done using, for example, customary phase detectors. Alternatively, it is also possible to calculate the gas proportion from the heat flow supplied to the evaporator and the material properties. The heat flow supplied can be derived, for example, from the temperature difference and mass flow of a heat-transfer medium used for heating between the inlet and the outlet, or else via the temperature difference between the average wall temperature and the temperature of the material stream comprising $C_3$ to $C_5$ hydrocarbons that is being vaporized.

Either a separate evaporator may be used for the vaporization or the evaporator used is a vaporization component within the reactor for the selective hydrogenation.

When a separate evaporator is being used as the evaporator, it is possible to use any evaporator known to those skilled in the art with which a controlled vaporization may be carried out. The heat may be supplied either indirectly by means of a heat-transfer medium or alternatively through heating by means of an electric heating element. The heat-transfer medium used may be any customary heat-transfer medium, for example steam or thermal oils. Examples of suitable evaporators are shell-and-tube heat exchangers, falling-film evaporators or thin-film evaporators. The preferred option, however, is to heat the material stream comprising $C_3$ to $C_5$ hydrocarbons at elevated pressure and then depressurize it in the reactor, which is operated at lower pressure. This can be done using, for example, a relief valve.

In an alternative embodiment, steps (a) and (b) are carried out in an apparatus having a vaporization part and a reaction part holding the catalyst bed comprising the hydrogenation catalyst, wherein the design of the vaporization part is such that, before entry into the catalyst bed, the material stream comprising $C_3$ to $C_5$ hydrocarbons is vaporized to an extent that 2 to 50 mol %, preferably 3 to 30 mol %, and in particular 5 to 25 mol %, of the material stream comprising $C_3$ to $C_5$ hydrocarbons is present in the gas phase.

The apparatus used may be one having a vaporization part and a reaction part, for example an apparatus having a vaporization part in the lower part and the reaction part in the upper part. The vaporization part is, for example, a shell-and-tube evaporator or a double-jacketed section through which a heat-transfer medium may be passed. Alternatively, it is also possible to provide electric heating. The reaction part is arranged above the vaporization part. This preferably comprises a fixed bed holding the hydrogenation catalyst.

As an alternative to the partial vaporization of the entire material stream comprising $C_3$ to $C_5$ hydrocarbons, it is also possible for vaporization of part of the material stream comprising $C_3$ to $C_5$ hydrocarbons in step (a) to be done by splitting the material stream comprising $C_3$ to $C_5$ hydrocarbons into two streams, completely vaporizing one of the two streams, and mixing this again with the second of the two streams after vaporization.

By splitting the material stream comprising $C_3$ to $C_5$ hydrocarbons into two parts, completely vaporizing one part, and then mixing the two streams, the proportion of the vaporized part is determined by the size of the substream that is being vaporized. This has the advantage that a substream is completely vaporized, which means there is no need to ensure that only enough heat is supplied for vaporization in order that the required proportion of the material stream is vaporized. It is therefore merely necessary to ensure that the material stream comprising $C_3$ to $C_5$ hydrocarbons is split into material streams of the required size. Since one stream is being completely vaporized, all that is necessary here is to ensure that the stream is actually vaporized completely and not just partially. To prevent the vaporized substream from immediately recondensing after mixing with the non-vaporized stream, it is further preferable when the second substream that is not vaporized is heated to a temperature just below, preferably 1 to 10° C. below, the vaporization temperature of the material stream comprising $C_3$ to $C_5$ hydrocarbons. Alternatively, the chosen size of the material stream to be vaporized needs to be large enough for there to still be an adequately large gas phase present after mixing and condensing.

The substream may be vaporized in any desired evaporator. Suitable evaporators correspond to those mentioned above for the embodiment in which the entire material stream comprising $C_3$ to $C_5$ hydrocarbons is supplied to the evaporator.

For the adjustment of the vaporized proportion in the material stream comprising $C_3$ to $C_5$ hydrocarbons, it is additionally possible, when using a separate evaporator for the vaporization, to connect a phase separator downstream of the evaporator. In the phase separator, the gas phase and the liquid phase are separated from one another and withdrawn separately. The proportion of the gas phase in the material stream comprising $C_3$ to $C_5$ hydrocarbons may then be achieved by mixing appropriate proportions of the gas phase and liquid phase. If the proportion of the liquid phase is too large, part of the liquid phase is withdrawn and returned to the evaporator. Similarly, if the gas phase is too large, part of the gas phase is withdrawn and returned. This allows the proportions of the material streams in the gas phase and in the liquid to be adjusted and mixed such that the proportion of the gas phase in the mixed material stream that is then supplied to the reactor is in the range from 2 to 50 mol %, preferably 3 to 30 mol %, and in particular 5 to 25 mol %.

Particularly when vaporization is carried out in a separate evaporator rather than using an apparatus that comprises a vaporization part and a reaction part, that is to say both in the embodiment in which the entire material stream comprising $C_3$ to $C_5$ hydrocarbons is supplied to an evaporator or, alternatively, in the embodiment in which the material stream comprising $C_3$ to $C_5$ hydrocarbons is split and one part is vaporized, a further part of the material stream comprising $C_3$ to $C_5$ hydrocarbons may vaporize on entering the reactor. This is the case particularly when the pressure in the reactor is lower than the pressure of the material stream in the feed line before entering the reactor.

When part of the material stream vaporizes on entering the reactor, i.e. when the reaction step comprises a separate reactor, the vaporization in step (a) is controlled such that, on entry of the material stream comprising $C_3$ to $C_5$ hydrocarbons into the reactor, a further part vaporizes, with the result that, after entry of the material stream comprising $C_3$ to $C_5$ hydrocarbons into the reactor, 2 to 50 mol %, preferably 3 to 30 mol %, and in particular 5 to 25 mol %, of the material stream comprising $C_3$ to $C_5$ hydrocarbons is present in the gas phase.

It is particularly preferable when vaporization of part of the material stream comprising $C_3$ to $C_5$ hydrocarbons is carried out entirely on entering the reactor. In this case, rather than an evaporator connected upstream of the reactor there is a heat exchanger that heats the material stream comprising $C_3$ to $C_5$ hydrocarbons, with this heating being to a temperature that is below the boiling point. The pressure at which the material stream comprising $C_3$ to $C_5$ hydrocarbons is heated is higher than the pressure in the reactor. Heat exchangers of this type are also referred to as forced-circulation flash evaporators.

The reactor used for the selective hydrogenation may be any reactor known to those skilled in the art that is suitable for selective hydrogenations. Examples of such reactors are fixed-bed reactors in which the hydrogenation catalyst is installed as a fixed bed. Particular preference is given to fixed-bed reactors that are charged with the reactants from above, so-called "trickle-flow reactors".

Examples of suitable hydrogenation catalysts are those comprising at least one metal of group VIII of the periodic table (Fe, Ru, Os, Co, Rh, Ir, Ni, Pd, Pt) as the hydrogenation metal, in particular palladium, and optionally also a promoter on an oxidic support.

The catalyst preferably has a diameter of 1.5 to 10 mm, more preferably 1.5 to 5 mm, and in particular 2.5 to 3.5 mm.

Preference is given to using a catalyst in which the metal of group VIII of the periodic table forms a shell structure in the catalyst.

The designation of the groups in the periodic table is in accordance with the CAS (Chemical Abstracts Service) nomenclature.

The catalyst may additionally comprise at least one promoter. This may, for example, be other metals of groups VIII, IB, and IIB of the periodic table (Cu, Ag, Au, Zn, Cd, Hg). In a preferred embodiment, the catalyst comprises, in addition to the metal of group VIII of the periodic table, at least one metal from group IB of the periodic table. Particular preference is given to silver.

In a particularly preferred embodiment, the catalyst according to the invention comprises palladium and silver.

The catalyst may be of any desired shape, for example extrudates, hollow extrudates, tablets, rings, spherical particles or spheres. Preference is given to catalysts in the form of an extrudate.

The metals may be in pure metallic form or they may be in the form of compounds, for example in the form of metal oxides. Under the operating conditions of a hydrogenation process, they are generally in the form of metals. Any oxides may be converted into metals in a manner known to those skilled in the art prior to using the catalyst in a hydrogenation process; this may be done inside or outside a hydrogenation reactor, for example by pre-reduction and—if necessary or advantageous for manipulations with the pre-reduced catalyst—subsequent surface passivation.

The content in the catalyst of metal(s) of group VIII of the periodic table, in particular palladium, is preferably not less than 0.01% by weight, more preferably not less than 0.1% by weight, in particular not less than 0.15% by weight. This content is preferably not more than 5% by weight, more preferably not more than 1% by weight, in particular not more than 0.6% by weight. Although lower and higher contents are possible, they are usually economically unsatisfactory because of excessively low activity or excessively high raw material costs. In a particularly preferred embodiment, only one hydrogenation metal, in particular palladium, is used.

The proportion of the amounts of hydrogenation metal of group VIII of the periodic table and additives or dopants is a parameter to be optimized in each individual case. The ratio of atoms of metal of group VIII of the periodic table, particularly preferably palladium, to the promoter, particularly preferably silver, is preferably 0.1-10, more preferably 2-7, in particular 2.5-6.

The oxidic support of the hydrogenation catalyst is preferably aluminum oxide, particularly preferably in a mixture of δ-, θ-, and α-aluminum oxide. In addition to unavoidable impurities, the support may also comprise other additives to a certain extent. For example, it may comprise other inorganic oxides such as oxides of metals of groups IIA, IIIB, IVB, IIIA, and IVA of the periodic table, in particular silicon dioxide, titanium dioxide, zirconium dioxide, zinc oxide, magnesium oxide, sodium oxide, and calcium oxide. The maximum content in the support of such oxides other than aluminum oxide depends on the oxide actually present, but can be determined in the individual case on the basis of the X-ray diffraction pattern of the hydrogenation catalyst, since a change in the structure is accompanied by a significant change in the X-ray diffraction pattern. In general, the content of such oxides other than aluminum oxide is below 50% by weight, preferably below 30% by weight, more preferably below 10% by weight. The degree of purity of the aluminum oxide is preferably higher than 99%.

Examples of appropriate catalysts and suitable processes for the preparation thereof are described in WO-A 2006/040159 or in WO-A 2006/040160.

In addition to the material stream comprising $C_3$ to $C_5$ hydrocarbons, hydrogen is supplied to the reactor for the selective hydrogenation. The amount of hydrogen is, according to the invention, in the range from 2 to 20 moles per mole of diene present in the material stream comprising $C_3$ to $C_5$ hydrocarbons. The hydrogen may be added either directly to the hydrogenation reactor or alternatively to the material stream comprising $C_3$ to $C_5$ hydrocarbons. In this case, the addition may take place either before vaporizing, mixing or condensing in step (a) or alternatively after vaporizing, mixing or condensing. When the hydrogen is added to the material stream comprising $C_3$ to $C_5$ hydrocarbons, this also acts as a gas that can be used to adjust the proportion of the gaseous proportion of the material stream comprising $C_3$ to $C_5$ hydrocarbons.

The pressure in the hydrogenation reactor used to carry out the selective hydrogenation is preferably in the range from 2 to 20 bar, preferably from 2.2 to 7 bar, and the inlet temperature of the material stream comprising $C_3$ to $C_5$ hydrocarbons is from 0 to 80° C., preferably 20 to 60° C. When the material stream comprising $C_3$ to $C_5$ hydrocarbons is depressurized during addition to the hydrogenation reactor for vaporization, the heating of the material stream comprising $C_3$ to $C_5$ hydrocarbons is preferably carried out at a pressure that is 0.5 to 8 bar, more preferably in the range from 0.5 to 5 bar, and in particular in the range from 0.5 to 3.5 bar, above the pressure in the hydrogenation reactor.

Preference is given to carrying out the selective hydrogenation at a pressure in the range from 2 to 20 bar, and in particular at a pressure in the range from 2 to 12 bar, and at an inlet temperature of the material stream comprising $C_3$ to $C_5$ hydrocarbons in the range from 0 to 80° C., and in particular in the range from 20 to 60° C.

The selective hydrogenation generally gives rise to a liquid phase as the product stream that comprises the $C_3$ to $C_5$ alkenes having precisely one double bond in the desired concentration. However, $C_3$ to $C_5$ alkenes having precisely one double bond may additionally be present in the gas phase too. In order to obtain this too as a product stream, it is preferable to cool the gas phase such that the $C_3$ to $C_5$ alkenes having precisely one double bond that are present in the gas phase condense and can likewise be withdrawn as product.

The process according to the invention is particularly suitable for removing dienes from material streams comprising $C_3$ to $C_5$ hydrocarbons that already comprise a high proportion of $C_3$ to $C_5$ alkenes having precisely one double bond and in which the proportion of $C_3$ to $C_5$ alkenes having precisely one double bond must not fall below a specified concentration in order to meet a defined specification. The process is particularly suitable for removing dienes from material streams comprising $C_3$ to $C_5$ hydrocarbons that comprise not less than 99% by weight of $C_3$ to $C_5$ alkenes having precisely one double bond.

In customary selective hydrogenation processes, particularly when removing dienes from a material stream that has a correspondingly high proportion of alkenes having precisely one double bond, it cannot be ruled out that the content of desired alkenes having precisely one double bond will likewise be reduced by side reactions, for example overhydrogenations or isomerizations, with the result that, in the product stream after the selective hydrogenation, the proportion of $C_3$ to $C_5$ alkenes having precisely one double bond no longer meets the defined specification but is below this. The process according to the invention makes it possible to selectively hydrogenate a material stream comprising not less than 99% by weight of $C_3$ to $C_5$ alkenes having precisely one double bond such that the product stream likewise comprises not less than 99% by weight of $C_3$ to $C_5$ alkenes having precisely one double bond.

In a particularly preferred embodiment, the $C_3$ to $C_5$ alkene having precisely one double bond is a butene and in particular but-1-ene. The diene in this case is accordingly butadiene and possibly pentadiene, in particular butadiene. When the desired alkene having precisely one double bond is but-1-ene, the unwanted by-products that can form in this case are in particular but-2ene and n-butane.

In addition to diene, the material stream comprising $C_3$ to $C_5$ hydrocarbons generally comprises other components as impurities, generally hydrocarbons having a number of carbon atoms that is larger or smaller than desired, for example $C_2$ hydrocarbons in the case of a material stream comprising $C_3$ to $C_5$ hydrocarbons as the target product or else hydrocarbons having more than 5 carbons, for example $C_6$ to $C_8$ hydrocarbons.

When the target product is a butene, in particular but-1-ene, $C_3$ or $C_5$ hydrocarbons may also be present for example in the material stream as secondary components.

However, when using butene as a (co-)monomer in a polymerization reaction, dienes and especially butadiene are particularly problematic by-products, as they affect polymer crosslinking. For this reason, it is necessary to remove butadiene from the material stream without departing from the defined specification for the polymerization, i.e. the content of butenes, in particular but-1-ene. This means that overhydrogenation or isomerization must be absent or occur only to a very minimal degree in the selective hydrogenation. Particularly when but-1-ene is the target product, butadiene must be removed without increasing the content of but-2-ene or butane (for example through isomerization or overhydrogenation of but-1-ene) to values above the specified limits.

The process according to the invention is also particularly suitable for further reducing the proportion of dienes from an already-processed material stream comprising $C_3$ to $C_5$ hydrocarbons that still comprises traces of dienes. The diene content in such material streams is generally less than 1000 ppm. The process is particularly suitable for removing dienes by selective hydrogenation from a material stream comprising $C_3$ to $C_5$ hydrocarbons in which the diene content is less than 500 ppm and in particular less than 200 ppm.

EXAMPLES 2.5 kg/h of a material stream having a but-1-ene content of 99.84 and containing 121 ppm and 182 ppm of butadiene was hydrogenated in a trickle-bed reactor holding 200 ml of a palladium/silver catalyst, obtainable for example as H0-43 from BASF SE, as hydrogenation catalyst. Before admission of the material stream to the trickle-bed reactor, the material stream was heated in an electrically operated evaporator and partially vaporized. The heat supply was adjusted such that about 15% by weight of the material stream used was present in the gas phase after vaporization.

The reaction was carried out such that the temperature at the reactor inlet was 40° C. or alternatively 30° C. The temperature at the reactor inlet was adjusted via the pressure at the reactor outlet.

The tables below show the composition of the product stream obtained in the selective hydrogenation, the proportion of hydrogen supplied, the temperature at the reactor inlet, and the pressure at the reactor outlet. Table 1 lists the process parameters for the individual examples and table 2 shows the respective composition of the product stream withdrawn from the trickle-bed reactor.

For examples 1 and 2, a feed stream was used that comprised 99.84% by weight of but-1-ene, 370 ppm of n-butane, 92 ppm of trans-but-2-ene, 112 ppm of cis-but-2-ene, and 121 ppm of butadiene; for examples 3, 4, and 5, a feed stream comprising 99.84% by weight of but-1-ene, 358 ppm of n-butane, 95 ppm of trans-but-2-ene, 112 ppm of cis-but-2-ene, and 182 ppm of butadiene was used. The remainder is mainly $C_3$ and $C_5$ hydrocarbons present as impurities and also other common impurities that arise in butene production.

TABLE 1

Process parameters

| | Proportion in the gas phase in feed stream [wt.-%] | Ratio $H_2$/ butadiene [mol/mol] | Pressure at reactor outlet [bar(g)] | Temperature at reactor inlet [° C.] |
|---|---|---|---|---|
| Example 1 | 15 | 4.7 | 3.17 | 40 |
| Example 2 | 14 | 4.7 | 2.20 | 30 |
| Example 3 | 15 | 2.1 | 3.17 | 40 |
| Example 4 | 15 | 5.0 | 3.17 | 40 |
| Example 5 | 15 | 3.1 | 3.17 | 40 |

TABLE 2

Composition of the product stream

| | But-1-ene [wt.-%] | n-Butane [ppm] | trans-But-2-ene [ppm] | cis-But-2-ene [ppm] | Butadiene [ppm] |
|---|---|---|---|---|---|
| Example 1 | 99.73 | 441 | 705 | 668 | 2 |
| Example 2 | 99.81 | 391 | 242 | 252 | 65 |
| Example 3 | 99.78 | 435 | 435 | 362 | 30 |
| Example 4 | 99.55 | 656 | 1524 | 1421 | not detectable |
| Example 5 | 99.78 | 396 | 473 | 435 | 10 |

The examples show clearly that, by adjusting the proportion in the gas phase, it is possible to carry out a selective hydrogenation in which the butadiene reacts through hydrogenation. The proportion of but-1-ene can moreover be seen to decrease only slightly. The largest decrease in the but-1-ene content is seen when the hydrogen supply is increased. However, even here the but-1-ene content falls by only 0.29%, resulting in a 0.3% decrease in the material stream. On lowering the hydrogen proportion, a satisfactory decrease in the butadiene content can still be observed, alongside an even smaller decrease in the but-1-ene content.

A satisfactory product stream was obtained for a required specification for but-1-ene of 99.5% by weight.

The invention claimed is:

1. A process for removing dienes from a material stream comprising C3 to C5 hydrocarbons by selective hydrogenation at a specified reaction pressure and a specified reaction temperature in the presence of a hydrogenation catalyst by feeding the material stream via a reactor inlet into a reactor and contacting the material stream with the hydrogenation catalyst in the reactor to produce a product stream comprising a reduced amount of dienes, wherein the reaction pressure and the reaction temperature at the reactor inlet are regulated such that the reaction pressure at the reactor inlet does not deviate by more than 0.01 bar from the specified reaction pressure and the reaction temperature at the reactor inlet does not deviate by more than 0.1° C. from the specified reaction temperature and the proportion of hydrogen supplied to the selective hydrogenation is in a range from 2 to 20 moles per mole of diene present in the material stream comprising C3 to C5 hydrocarbons.

2. The process according to claim 1, wherein the material stream comprising C3 to C5 hydrocarbons comprises not less than 99% by weight of C3 to C5 alkenes having precisely one double bond.

3. The process according to claim 2, wherein the C3 to C5 alkenes having precisely one double bond is but-1-ene.

4. The process according to claim 1, wherein a product stream comprises not less than 99% by weight of C3 to C5 alkenes having precisely one double bond.

5. The process according to claim 1, wherein the diene content in the material stream comprising C3 to C5 hydrocarbons is less than 1000 ppm.

6. A process for removing dienes from a material stream comprising C3 to C5 hydrocarbons by selective hydrogenation at a specified reaction pressure and a specified reaction temperature in the presence of a hydrogenation catalyst by feeding the material stream via a reactor inlet into a reactor and contacting the material stream with the hydrogenation catalyst in the reactor to produce a product stream comprising a reduced amount of dienes, wherein the reaction pressure and the reaction temperature at the reactor inlet are regulated such that the reaction pressure at the reactor inlet does not deviate by more than 0.01 bar from the specified reaction pressure and the reaction temperature at the reactor inlet does not deviate by more than 0.1° C. from the specified reaction temperature and the proportion of hydrogen supplied to the selective hydrogenation is in a range from 2 to 20 moles per mole of diene present in the material stream comprising C3 to C5 hydrocarbons, wherein for regulating the pressure and the temperature at the reactor inlet, the process comprises:
  (a) obtaining a partially vaporized material stream comprising C3 to C5 hydrocarbons by one of:
    (i) vaporizing a part of a material stream comprising liquid C3 to C5 hydrocarbons,
    (ii) mixing a gaseous material stream comprising C3 to C5 hydrocarbons and a liquid material stream comprising C3 to C5 hydrocarbons, or
    (iii) condensing a part of a material stream comprising gaseous C3 to C5 hydrocarbons,
  wherein 2 to 50 mol % of the partially vaporized material stream comprising C3 to C5 hydrocarbons is present in the gas phase,
  (b) supplying the partially vaporized material stream comprising C3 to C5 hydrocarbons to the reactor comprising the hydrogenation catalyst and adding hydrogen in a proportion of 2 to 20 moles per mole of diene present in the material stream comprising C3 to C5 hydrocarbons to obtain a hydrogenated partially vaporized material stream comprising C3 to C5 hydrocarbons, wherein the hydrogenated partially vaporized material stream contains a reduced amount of dienes, relative to the partially vaporized material stream, wherein the hydrogen is added together with the partially vaporized material stream comprising C3 to C5 hydrocarbons or via a separate addition point,
  (c) separating the hydrogenated partially vaporized material stream into a gas phase stream and a liquid phase stream and withdrawing the liquid phase stream as a product stream.

7. The process according to claim 6, wherein an inert gas is added to adjust the amount of the vaporized part of the material stream comprising C3 to C5 hydrocarbons.

8. The process according to claim 7, wherein the inert gas is selected from the group consisting of nitrogen, methane, carbon dioxide, noble gases, and mixtures thereof.

9. The process according to claim 6, wherein steps (a) and (b) are carried out in an apparatus having a vaporization part and a reaction part holding a catalyst bed comprising the hydrogenation catalyst, wherein the design of the vaporization part is such that, before entry into the catalyst bed, the material stream comprising C3 to C5 hydrocarbons is vaporized to an extent that 2 to 50 mol % of the material stream comprising C3 to C5 hydrocarbons is present in the gas phase.

10. The process according to claim 6, wherein the vaporization of the part of the material stream comprising C3 to C5 hydrocarbons in step (a) is done by splitting the material stream comprising C3 to C5 hydrocarbons into two streams, completely vaporizing one of the two streams, and mixing the completely vaporized stream of the two streams with the remaining stream of the two streams after the vaporization.

11. The process according to claim 6, wherein for obtaining the partially vaporized material stream, the material stream comprising C3 to C5 hydrocarbons is heated at an elevated pressure and then depressurized in the reactor, which is operated at a lower pressure.

12. The process according to claim 6, wherein the vaporization in step (a) and the reaction step in step (b) are carried out in separate units and the vaporization in step (a) is controlled such that, on entry of the partially vaporized material stream comprising C3 to C5 hydrocarbons into the reactor, a further part vaporizes, such that, after entry of the partially vaporized material stream comprising C3 to C5 hydrocarbons into the reactor, 2 to 50 mol % of the partially vaporized material stream comprising C3 to C5 hydrocarbons is present in the gas phase.

13. The process according to claim 6, wherein the gas phase stream obtained in step (c) is cooled, resulting in condensation of C3 to C5 alkenes having precisely one double bond that are present in the gas phase and withdrawal of the condensed C3 to C5 alkenes having precisely one double bond as product.

* * * * *